United States Patent
Cho et al.

(10) Patent No.: US 6,620,936 B2
(45) Date of Patent: Sep. 16, 2003

(54) 9-AMINOACRIDINE DERIVATIVES AND PROCESS FOR THE PREPARATION THEREOF

(75) Inventors: Eui-Hwan Cho, Seoul (KR); Sun-Gan Chung, Kyungki-do (KR); Sun-Hwan Lee, Kyungki-do (KR); Ho-Seok Kwon, Kyungki-do (KR); Dong-Wook Kang, Kyungki-do (KR); Jeong-Ho Joo, Kyungki-do (KR)

(73) Assignee: Samjin Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 09/855,530

(22) Filed: May 16, 2001

(65) Prior Publication Data

US 2002/0111491 A1 Aug. 15, 2002

Related U.S. Application Data

(63) Continuation of application No. 09/640,400, filed as application No. PCT/KR99/00787 on Dec. 17, 1999, now abandoned.

(30) Foreign Application Priority Data

Dec. 18, 1998 (KR) .............................................. 98-56185

(51) Int. Cl.[7] ..................... C07D 219/10; A61K 31/473; A61P 35/00
(52) U.S. Cl. ......................... 546/106; 546/105; 514/297
(58) Field of Search ................................ 546/105, 106; 514/297

(56) References Cited

U.S. PATENT DOCUMENTS 5,229,395 A * 7/1993 Watanabe et al.
5,354,864 A * 10/1994 Watanabe et al.

\* cited by examiner

*Primary Examiner*—Evelyn Mei Huang
(74) *Attorney, Agent, or Firm*—Birch, Stewart, Kolasch & Birch, LLP

(57) ABSTRACT

The present invention relates to new 9-aminoacridine derivatives of general formula (I), wherein A is hydrogen or (II) (wherein X is oxygen or sulfur, $R_1$, $R_2$, $R_3$, $R_4$ and $R_5$ are independently hydrogen, halogen, nitro, amino, hydroxy, $C_1$–$C_4$ lower alkylhydroxy, $C_1$–$C_4$ lower alkylamino, $C_1$–$C_8$ alkyl, $C_1$–$C_4$ lower alkoxy or $C_1$–$C_4$ lower alkyloxycarbonyl and m and n are independently an integer of 0, 1 or 2), $R_6$, $R_7$, $R_8$ and $R_9$ are independently $C_1$–$C_8$ alkyl or $C_1$–$C_4$ lower alkoxy, and Y is hydrogen, amino, —N=CHR' (wherein R' is hydrogen, benzyl, $C_1$–$C_8$ alkyl or $C_1$–$C_6$ lower alkylamino), (III) (wherein R" is hydrogen, benzyl, $C_1$–$C_8$ alkyl or $C_1$–$C_6$ lower alkylamino, and R'" is hydrogen, benzyl, $C_1$–$C_8$ alkyl or amino protecting group) or (IV) (wherein, X is as defined above, $R_1'$, $R_2'$, $R_3'$, $R_4'$ and $R_5'$ are independently hydrogen, halogen, nitro, amino, hydroxy, $C_1$–$C_4$ lower alkylhydroxy, $C_1$–$C_4$ lower alkylamino, $C_1$–$C_8$ alkyl, $C_1$–$C_4$ lower alkoxy or $C_1$–$C_4$ lower alkylcarboxy, and q and r are independently an integer of 0, 1 or 2) or its pharmaceutically acceptable salt, and process for the preparation thereof.

4 Claims, No Drawings

9-AMINOACRIDINE DERIVATIVES AND PROCESS FOR THE PREPARATION THEREOF

CROSS REFERENCE TO RELATED APPLICATIONS

This application is a continuation of U.S. Ser. No. 09/640/400, filed Aug. 17, 2000, which is the national phase of International Application No. PCT/KR99/00787, filed Dec. 17, 1999, which claims priority from Korean Application No. 1998/56185, filed Dec. 18, 1998, the contents of which are incorporated herein by reference in their entirety.

The present invention relates to a new 9-aminoacridine derivative of the general formula (I)

(I)

wherein A is hydrogen or (wherein X is oxygen or sulfur, $R_1$, $R_2$, $R_3$, $R_4$ and $R_5$ are independently hydrogen, halogen, nitro, amino, hydroxy, $C_1$–$C_4$ lower alkylhydroxy, $C_1$–$C_4$ lower alkylamino, $C_1$–$C_8$ alkyl, $C_1$–$C_4$ lower alkoxy or $C_1$–$C_4$ lower alkoxycarbonyl and m and n are independently an integer of 0, 1 or 2),
$R_6$, $R_7$, $R_8$ and $R_9$ are independently $C_1$–$C_8$ alkyl or $C_1$–$C_4$ lower alkoxy,
and Y is hydrogen, amino, —N=CHR' (wherein R' is hydrogen, benzyl, $C_1$–$C_8$ alkyl or $C_1$–$C_6$ lower alkylamino), (wherein R" is hydrogen, benzyl, $C_1$–$C_8$ alkyl or $C_1$–$C_6$ lower alkylamino, and R'" is hydrogen, benzyl, $C_1$–$C_8$ alkyl or amino protecting group) or (wherein, X is as defined above, $R_1$, $R_2$, $R_3$, $R_4$, and $R_5$ are independently hydrogen, halogen, nitro, amino, hydroxy, $C_1$–$C_4$ lower alkylhydroxy, $C_1$–$C_4$ lower alkylamino, $C_1$–$C_8$ alkyl, $C_1$–$C_4$ lower alkoxy or $C_1$–$C_4$ lower alkyloxycarbonyl, and m and n are independently an integer of 0, 1 or 2) or its pharmaceutically acceptable salt.

In the above compounds of the formula (I) wherein Y is (R" and R'" are as defined above.), there may be isomers of l-form, d-form or racemic form.

In the above definitions, $C_1$–$C_8$ alkyl means straight or branched alkyl groups such as methyl, ethyl, propyl, isopropyl, n-butyl, isobutyl, sec-butyl, pentyl, isopentyl, hexyl, heptyl, octyl and 2-methylpentyl.

$C_1$–$C_4$ lower alkoxy means methoxy, ethoxy, propoxy, isopropoxy, butoxy, isobutoxy, tert-butoxy or the like.

$C_1$–$C_4$ lower alkylcarboxy means an esterified carboxy by a lower alkyl.

$C_1$–$C_4$ lower alkylamino means methylamino, ethylamino, propylamino, butylamino or the like.

$C_1$–$C_4$ lower alkylhydroxy means methylhydroxy, ethylhydroxy, propylhydroxy or the like.

Amino protecting group may include benzyl, benzyloxycarbonyl, t-butoxycarbonyl, 2,2,2-trichloroethoxycarbonyl, methoxycarbonyl and 2-methylsulfonylethoxycarbonyl.

The inventors had studied for a long time to find new compounds having intensive antitumor activities. As a result, the inventors have found out that the compounds of the general formula (I), or acid addition salts thereof as defined above have not only prominent antitumor activities but also very low toxicities.

Accordingly, an object of the invention is to provide a compound of the general formula (I) or acid addition salt thereof having not only prominent antitumor activity but also very low toxicity.

Another object of the invention is to provide a process for the preparation of the compound of the general formula (I) or acid addition salt thereof.

The compounds of the present invention can be mixed with pharmaceutically acceptable vehicles by a conventional method to give pharmaceutical preparations to be used for prevention or treatment of various kinds of tumors.

Therefore, the other object of the present invention is to provide pharmaceutical preparations containing an effective amount of a compound of the general formula (I) or acid addition salt thereof as an active ingredient.

Acids which can be reacted with the compound of the general formula(I) to form acid addition salt thereof are pharmaceutically acceptable inorganic acids, organic acids, amino acids or sulfonic acids; for example, inorganic acids such as hydrochloric acid, hydrobromic acid, sulfuric acid, phosphoric acid and nitric acid; organic acids such as formic acid, acetic acid, propionic acid, succinic acid, citric acid, maleic acid and malonic acid; amino acids such as serine, cysteine, cystine, asparagine, glutamine, lysine, arginine, tyrosine and proline; sulfonic acids such as methanesulfonic acid, ethanesulfonic acid, benzenesulfonic acid and toluenesulfonic acid.

Vehicles used in formulating pharmaceutical preparations containing the compound of the general formula (I) as an active ingredient are sweetening agents, binding agents, dissolving agents, aids for dissolution, wetting agents, emulsifying agents, isotonic agents, adsorbents, degrading, agents, antioxidants, preservatives, lubricating agents, fillers, perfume or the like; for example may include lactose, dextrose, sucrose, mannitol, sorbitol, cellulose, glycine, silica, talc, stearic acid, stearin, magnesium stearate, calcium stearate, magnesium aluminum silicate, starch, gelatine, tragacanth gum, glycine, silica, alginic acid, sodium alginate, methyl cellulose, sodium carboxy methyl cellulose, agar, water, ethanol, polyethylenglycol, polyvinyl pyrrolidone, sodium chloride, potassium chloride, orange essence, strawberry essence and vanilla aroma.

Daily dosage of the compound of the general formula (I) may be varied depending on age, sex and degree of disease, but preferably 1 mg to 5,000 mg per day may be administered by once to several times.

The compound of the general formula (I) according to the present invention may be prepared by following schemes I, II or III.

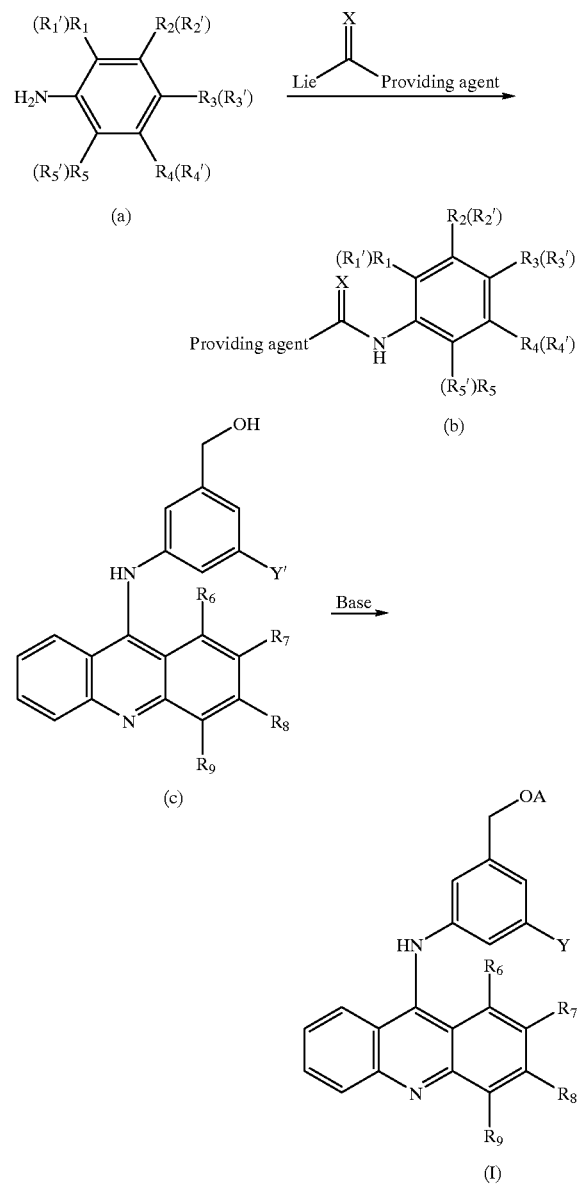

wherein $R_1$, $R_2$, $R_3$, $R_4$, $R_5$, $R_6$, $R_7$, $R_8$, $R_9$, $R_1'$, $R_2'$, $R_3'$, $R_4'$, $R_5'$, A and Y are as defined above, Y' is H or $NH_2$, and Lie is a leaving group such as hydrogen and halogen atom.

According to the above scheme, a compound of the general formula (a) is reacted with a —C(=X)— group-providing agent in organic solvent to give a compound of the general formula (b), and successively the compound (b) is reacted with a compound of the general formula (c) to give a compound of the general formula (I).

The —C(=X)— group-providing agent used may include, for example, 1,1-carbonyldiimidazole, 1,1-carbonylthiodiimidazole, phosgene, thiophosgene, carbonyldiphenoxide and phenylchloroformate, and it may be used in an amount of 1–1.5 equivalent, preferably 1–1.1 equivalent to the starting compound.

The reaction may be carried out preferably in a conventional organic solvent such as tetrahydrofuran, dichloromethane, chloroform, acetonitrile and dimethylformamide.

In addition, the reaction may be carried out preferably in the presence of a coupling agent. Such coupling agent may include conventional inorganic or organic bases, for example, including sodium hydride, potassium hydride, sodium hydroxide, potassium hydroxide, sodium carbonate, potassium carbonate, cesium carbonate, sodium bicarbonate, potassium bicarbonate, triethylamine, pyridine and DBU, and it may be used by 1–5 equivalents.

The reaction may be carried out at a temperature between 3° C. and boiling point of a used solvent, preferably at 50° C.–100° C. for 5–48 hours, preferably for 10–24 hours.

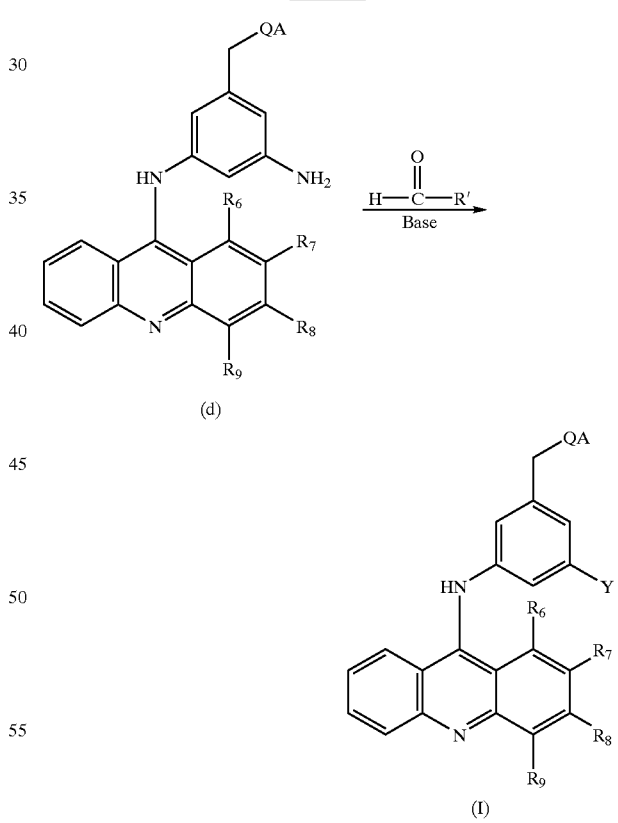

wherein, $R_6$, $R_7$, $R_8$, $R_9$, R', A and Y are as defined above.

According to the above scheme II, a compound of the general formula (d) above may be reacted with HCOR' in the presence of a base and a conventional organic solvent to give a compound of the general formula (I).

In the above reaction, the conventional organic solvent may include tetrahydrofuran, dichloromethane, chloroform, acetonitrile and dimethylformamide.

In addition, the reaction is carried out in the presence of a conventional inorganic or organic base as a coupling agent, and such a conventional base may include sodium hydride, potassium hydride, sodium hydroxide, potassium hydroxide, sodium carbonate, potassium carbonate, cesium carbonate, sodium bicarbonate, potassium bicarbonate, triethylamine, pyridine and DBU, and maybe used in an amount of 1–5 equivalents.

The reaction may be carried out at a temperature between 3° C. and boiling point of the solvent used, preferably at 50° C.–100° C. for 5–48 hours, preferably for 10–24 hours.

Scheme III

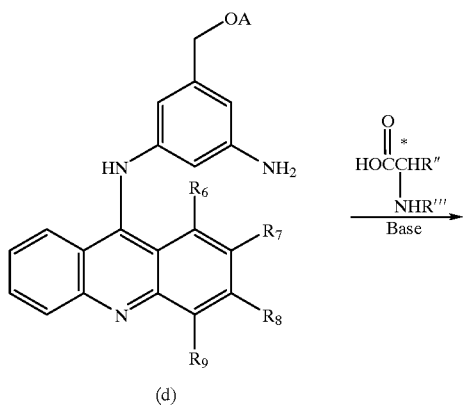

(d)

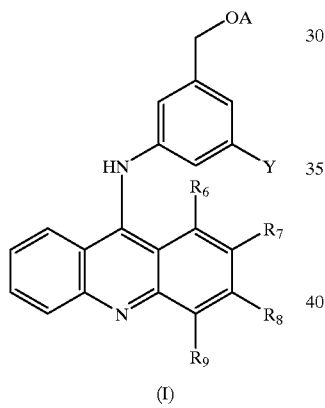

(I)

wherein, $R_6$, $R_7$, $R_8$, $R_9$, R″, R‴, A and Y are as defined above.

According to the above scheme III, a compound of the general formula (d) may be reacted with a compound of following formula,

in the presence of a base and a conventional organic solvent to give a compound of the general formula (I).

The resulting compound of the formula (I) according to the scheme III may have isomers of l-form, d-form or racemic form.

In the above reaction, the conventional organic solvent may include tetrahydrofuran, dichloromethane, chloroform, acetonitrile and dimethylformamide.

And also the reaction is carried out preferably in the presence of a conventional organic or inorganic base as a coupling agent, and such a base may include sodium hydride, potassium hydride, sodium hydroxide, potassium hydroxide, sodium carbonate, potassium carbonate, cesium carbonate, sodium bicarbonate, potassium bicarbonate, triethylamine, pyridine and DBU, and it may be used in an amount of 1–5 equivalents.

The reaction may be carried out at a temperature between 3° C. and boiling point of the solvent used, preferably at 50° C.–100° C. for 5–48 hours, preferably for 10–24 hours.

In the above processes according to the present invention, in case any acid material is formed, a suitable basic material may be added before reaction in order to eliminate the acid material from the reaction system. Such a basic material may be alkali metal hydroxide, alkali earth metal hydroxide, alkali metal oxide, alkali earth metal oxide, alkali metal carbonate, alkali earth metal carbonate, alkali metal hydrogen carbonate, alkali earth metal hydrogen carbonate such as sodium hydroxide, potassium hydroxide, calcium hydroxide, magnesium hydroxide, magnesium oxide, calcium oxide, potassium carbonate, sodium carbonate, calcium carbonate, magnesium carbonate, magnesium bicarbonate, sodium bicarbonate and calcium bicarbonate, or organic amines.

The compound of the general formula (c) is a known compound, described in, for example, J. Med. Chem., 1995, 38, 3226 or may be prepared in a similar method thereto.

EXAMPLES

Compounds of the general formula (I) were prepared according to the above-mentioned processes of the invention.

(I)

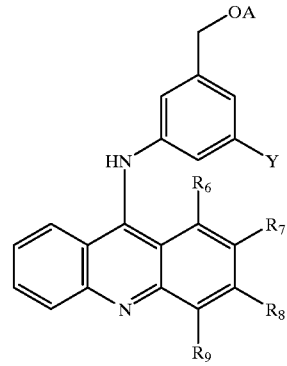

Examples 1–29

A compound of the general formula (I) wherein

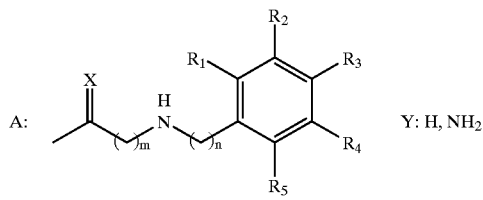

Y: H, NH₂

| Ex. No. | X | m | n | R₁ | R₂ | R₃ | R₄ | R₅ | R₆ | R₇ | R₈ | R₉ | Y |
|---|---|---|---|---|---|---|---|---|---|---|---|---|---|
| 1 | O | 0 | 0 | H | H | H | H | H | H | H | H | H | NH₂ |
| 2 | O | 0 | 0 | H | OCH₃ | H | H | H | H | H | H | H | NH₂ |
| 3 | O | 0 | 0 | H | OCH₃ | H | OCH₂ | H | H | H | H | H | NH₂ |
| 4 | O | 0 | 0 | H | OCH₃ | OCH₃ | OCH₃ | H | H | H | H | H | NH₂ |
| 5 | O | 0 | 0 | H | H | CH₃ | H | H | H | H | H | H | NH₂ |
| 6 | O | 0 | 0 | H | CH₃ | H | CH₃ | H | H | H | H | H | NH₂ |
| 7 | O | 0 | 0 | H | F | H | H | H | H | H | H | H | NH₂ |
| 8 | O | 0 | 0 | H | H | F | H | H | H | H | H | H | NH₂ |
| 9 | O | 0 | 0 | F | H | H | F | H | H | H | H | H | NH₂ |
| 10 | O | 0 | 0 | F | H | F | H | H | H | H | H | H | NH₂ |
| 11 | O | 0 | 0 | H | F | F | H | H | H | H | H | H | NH₂ |
| 12 | O | 0 | 0 | H | F | H | F | H | H | H | H | H | NH₂ |
| 13 | O | 0 | 0 | Cl | H | H | H | H | H | H | H | H | NH₂ |
| 14 | O | 0 | 0 | H | Cl | H | H | H | H | H | H | H | NH₂ |
| 15 | O | 0 | 0 | H | Cl | H | Cl | H | H | H | H | H | NH₂ |
| 16 | O | 0 | 0 | H | OH | H | H | H | H | H | H | H | NH₂ |
| 17 | S | 0 | 0 | H | OCH₃ | H | H | H | H | H | H | H | NH₂ |
| 18 | S | 0 | 0 | H | OCH₃ | H | OCH₃ | H | H | H | H | H | NH₂ |
| 19 | S | 0 | 0 | H | OCH₃ | OCH₃ | OCH₃ | H | H | H | H | H | NH₂ |
| 20 | O | 0 | 0 | H | OCH₃ | H | H | H | H | H | H | H | H |
| 21 | O | 0 | 0 | H | OCH₃ | H | OCH₃ | H | H | H | H | H | H |
| 22 | O | 0 | 0 | H | OCH₃ | OCH₃ | OCH₃ | H | H | H | H | H | H |
| 23 | O | 0 | 0 | H | F | H | F | H | H | H | CH₃ | CH₃ | NH₂ |
| 24 | O | 0 | 0 | H | Cl | H | Cl | H | H | H | CH₃ | CH₃ | N$_{H2}$ |
| 25 | O | 0 | 0 | H | Cl | H | Cl | H | H | CH₃ | H | H | NH₂ |
| 26 | O | 0 | 0 | H | F | H | F | H | H | CH₃ | H | H | NH₂ |
| 27 | O | 0 | 0 | H | F | H | F | H | H | CH₃ | CH₃ | H | NH₂ |
| 28 | O | 0 | 0 | H | F | H | F | H | H | H | H | OCH₃ | NH₂ |
| 29 | O | 0 | 0 | H | Cl | B | Cl | H | H | H | H | OCH₃ | NH₂ |

Examples 30–34
A compound of the general formula (I) wherein

A: H, Y:

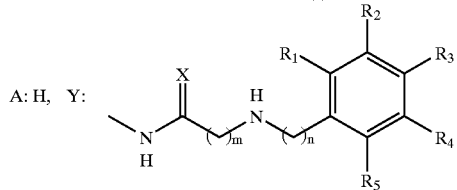

Examples 38~53
A compound of the general formula (I) wherein

A: H, Y:

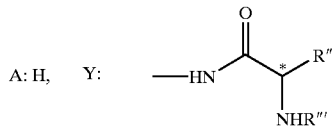

| Ex. No. | X | m | n | R₁' | R₂' | R₃' | R₄' | R₅' | R₆ | R₇ | R₈ | R₉ | A |
|---|---|---|---|---|---|---|---|---|---|---|---|---|---|
| 30 | O | 0 | 0 | H | F | H | F | H | H | H | H | H | H |
| 31 | O | 0 | 0 | H | F | H | H | H | H | H | H | H | H |
| 32 | O | 0 | 0 | H | Cl | H | Cl | H | H | H | H | H | H |
| 33 | O | 0 | 0 | H | F | H | F | H | H | H | H | OCH₃ | H |
| 34 | O | 0 | 0 | H | F | H | F | H | H | H | CH₃ | CH₃ | H |

(m, n = integer)

Examples 35–37
A compound of the general formula (I) wherein

| Ex. No. | A | R' | R₆ | R₇ | R₈ | R₉ |
|---|---|---|---|---|---|---|
| 35 | H | CH₃ | H | H | H | H |
| 36 | H | CH₂CH₃ | H | H | H | H |
| 37 | H | CH₂CH₂CH₃ | H | H | H | H |

A: H,
Y: N = CHR' ,R

| Ex. No. | A | R" | R''' | $R_6$ | $R_7$ | $R_8$ | $R_9$ |
|---|---|---|---|---|---|---|---|
| 38 | H | H | —C(=O)—O—C(CH₃)₃ | H | H | H | H |
| 39 | H | CH₃ | // | H | H | H | H |
| 40 | H | CH₂Ph | // | H | H | H | H |
| 41 | H | CH(CH₃)₂ | // | H | H | H | H |
| 42 | H | CH₂CH(CH₃)₂ | // | H | H | H | H |
| 43 | H | CH(CH₃)CH₂CH₃ | // | H | H | H | H |
| 44 | H | H | H | H | H | H | H |
| 45 | H | CH₃ | H | H | H | H | H |
| 46 | H | CH₂Ph | H | H | H | H | H |
| 47 | H | CH(CH₃)₂ | H | H | H | H | H |
| 48 | H | CH₂CH(CH₃)₂ | H | H | H | H | H |
| 49 | H | CH(CH₃)CH₂CH₃ | H | H | H | H | H |
| 50 | H | CH₃ | H | H | CH₃ | H | H |
| 51 | H | CH₃ | H | H | H | CH₃ | CH₃ |
| 52 | H | CH₃ | H | H | H | H | OCH₃ |
| 53 | H | CH₂CH₂CH₂CH₂NH₂ | H | H | H | H | H |

Example 1
[3-(acridin-9-yl)amino-5-amino]benzyl N-phenylcarbamate a) Phenyl N-carbamate Triethylamine (1.11 g, 11.0 mmol) was added to a solution of aniline (1.00 g, 11.0 mmol) dissolved in dichloromethane (20 ml), and phenylchloroformate (1.76 g, 11.0 mmol) was added thereto by dropping. The resulting solution was stirred for 2 hours at the room temperature, washed with distilled water, concentrated and purified by column chromatography to give the titled compound.

Yield: 81.7% m.p.: 119~120° C.

$^1$H NMR(CDCl$_3$): δ 5.10(1H,brs), 6.63(1H,dd), 6.67(2H, d), 7.05(1H,m), 7.13(2H,m), 7.46(2H,m), 7.60(2H,m)

b) [3-(acridin-9-yl)amino-5-amino]benzyl N-phenylcarbamate 3-(9-acridinylamino)-5-(hydroxymethyl)aniline (1.00 g, 3.17 mmol) and phenyl N-phenylcarbamate (0.67 g, 3.17 mmol) were dissolved in dimethylformaldehyde (40 ml), and thereto DBU (0.49 g, 3.17 mmol) was added by dropping. After stirring the resulting mixture for 12 hours at the room temperature, the used solvent was removed under the reduced pressure. The resulting product was purified by column chromatography to give the titled compound.

Yield: 62.5% m.p.: 98~100° C.

$^1$H NMR(DMSO-d$_6$): δ 5.03(2H,s), 6.13(1H,s), 6.35(2H, d), 6.99(1H,t), 7.25(2H,t), 7.46(9H,brs), 7.55(2H,brs), 8.09 (1H,brs)

Example 2
[3-(acridin-9-yl)amino-5-amino]benzyl N-(3-methoxyphenyl)carbamate 3-(9-acridinylamino)-5-(hydroxymethyl)aniline and phenyl N-(3-methoxylphenyl) carbamate were reacted by the same method to the example 1 to give the titled compound.

Yield: 57.4% m.p.: 83~86° C.

$^1$H NMR(DMSO-d$_6$): δ 3.74(3H,s), 5.01(2H,s), 6.11(1H, s), 6.14(1H,s), 6.35(2H,s), 6.73(2H,s), 7.55(3H,m), 8.45 (1H,s)

Example 3
[3-(acridin-9-yl)amino-5-amino]benzyl N-(3,5-dimethoxyphenyl)carbamate 3-(9-acridinylamino)-5-(hydroxymethyl)aniline and phenyl N-(3,5-dimethoxyphenyl) carbamate were reacted with the same method to the example 1 to give the titled compound.

Yield: 52.7% m.p.: 85~88° C.

$^1$H NMR(DMSO-d$_6$): δ 3.75(6H,s), 5.02(2H,s), 6.11(1H, s), 6.13(1H,s), 6.35(2H,s), 6.73(2H,s), 7.56(3H,m), 8.44 (1H,s)

Example 4
[3-(acridin-9-yl)amino-5-amino]benzyl N-(3,4,5-trimethoxyphenyl) carbamate 3-(9-acridinylamino)-5-(hydroxymethyl)aniline and phenyl N-(3,4,5-trimethoxyphenyl)carbamate were reacted with the same method to the example 1 to give the titled compound.

Yield: 47.6% m.p.: 120~122° C.

$^1$H NMR(DMSO-d$_6$): δ 3.71(3H,s), 3.79(6H,s), 5.00(2H, s), 6.08(1H,s), 6.23(1H,s), 6.32(1H,s), 6.85(2H,s), 7.12(2H, brs), 7.48(4H,brs), 8.17(2H,brs), 9.31(1H,s), 10.50 (1H,brs)

Example 5
[3-(acridin-9-yl)amino-5-amino]benzyl N-(4-methylpheny)carbamate 3-(9-acridinylamino)-5-(hydroxymethyl)aniline and phenyl N-(4-methylphenyl) carbamate were reacted with the same method to the example 1 to give the titled compound.

Yield: 54.9% m.p.: 95~97° C.

$^1$H NMR(DMSO-d$_6$): δ 2.62(3H,s), 5.08(2H,s), 5.94(1H, s), 6.08(1H,brs), 6.26(1H,s), 7.10(3H,d), 7.37(4H,d), 7.52 (2H,brs), 8.23(3H,brs), 9.62(1H,s), 10.8(1H,brs)

Example 6
[3-(acridin-9-yl)amino-5-amino]benzyl N-(3,5-dimethylphenyl) carbamate 3-(9-acridinylamino) -5-(hydroxymethyl) aniline and phenyl N-(3,5-dimethylphenyl) carbamate were reacted with the same method to the example 1 to give the titled compound.

Yield: 52.8% m.p.:118~121° C.

¹H NMR(DMSO-d₆): δ 2.24(6H,s), 4.98(2H,s), 6.05(1H, s), 6.22(1H,s), 6.32(1H,s), 6.60(1H,s), 7.09(4H,brs), 7.47 (4H,brs), 8.17(2H,brs), 9.24(1H,s), 10.5(1H,brs)

Example 7

[3-(acridin-9-yl)amino-5-amino]benzyl N-(3-fluorophenyl) carbamate 3-(9-acridinylamino)-5-(hydroxymethyl)aniline and phenyl N-(3-fluorophenyl) carbamate were reacted with the same method to the example 1 to give the titled compound.

Yield: 49.3% m.p.: 110~112° C.

¹H NMR(DMSO-d₆): δ 5.02(2H,s), 6.17(1H,s), 6.29(1H, s), 6.39(1H,s), 6.67(1H,brs), 7.09 (2H, brs), 7.19(2H,s), 7.39(1H,d), 7.54(3H,brs), 7.63(1H,brs), 8.08(2H,brs), 9.60 (1H,s)

Example 8

[3-(acridin-9-yl)amino-5-amino]benzyl N-(4-fluorophenyl) carbamate 3-(9-acridinylamino)-5-(hydroxymethyl)aniline and phenyl N-(4-fluorophenyl) carbamate were reacted with the same method to the example 1 to give the titled compound.

Yield: 48.9% m.p.: 161~163° C.

¹H NMR(DMSO-d₆): δ 5.02(2H,s), 6.13(1H,s), 6.33(2H, d), 6.93(2H,t), 7.11(2H,brs), 7.45(2H,brs), 7.53(2H,brs), 7.68(2H,brs), 8.07(2H,brs), 8.98(1H,brs)

Example 9

[3-(acridin-9-yl)amino-5-amino]benzyl N-(2,5-difluorophenyl) carbamate 3-(9-acridinylamino)-5-(hydroxymethyl)aniline and phenyl N-(2,5-difluorophenyl) carbamate were reacted with the same method to the example 1 to give the titled compound.

Yield: 46.8% m.p.: 188~193° C.

¹H NMR(DMSO-d₆): δ 5.06(2H,s), 6.23(1H,s), 6.38(1H, s), 6.42(1H,s), 6.68(1H,m), 7.01(1H,m), 7.15(2H,brs), 7.57 (2H,t), 7.82(3H,brs), 8.03(1H,s), 8.10(2H,d), 8.17(1H,brs)

Example 10

[3-(acridin-9-yl)amino-5-amino]benzyl N-(2,4-difluropheny) carbamate 3-(9-acridinylamino)-5-(hydroxymethyl)aniline and phenyl N-(2,4-difluorophenyl) carbamate were reacted with the same method to the example 1 to give the titled compound.

Yield: 47.0% m.p.: 100~102° C.

¹H NMR(DMSO-d₆): δ 5.03(2H,s), 6.17(1H,s), 6.32(1H, s), 6.39(1H,s), 6.85(2H,m), 7.10(2H,brs), 7.54(2H,brs), 7.66 (3H,brs), 7.78(1H,brs), 8.08(2H,brs), 8.54(1H,brs)

Example 11

[3-(acridin-9-yl)amino-5-amino]benzyl N-(3,4-difluorophenyl) carbamate 3-(9-acridinylamino)-5-(hydroxymethyl)aniline and phenyl N-(3,4-difluorophenyl) carbamate were reacted with the same method to the example 1 to give the titled compound.

Yield: 46.8% m.p.: 123~125° C.

¹H NMR(DMSO-d₆): δ 5.01(2H,s), 6.13(1H,s), 6.31(2H, s), 7.08(4H,m), 7.37(1H,s), 7.54 (3H, brs), 7.71 (1H, brs), 8.05 (2H, brs), 8. 8 6 (1H,brs)

Example 12

[3-(acridin-9-yl)amino-5-amino]benzyl N-(3,5-difluorophenyl) carbamate 3-(9-acridinylamino)-5-(hydroxymethyl)aniline and phenyl N-(3,5-difluorophenyl) carbamate were reacted with the same method to the example 1 to give the titled compound.

Yield: 46.5% m.p.; 125~128° C.

¹H NMR(DMSO-d₆): δ 5.01(2H,s), 6.13(1H,s), 6.27(1H, s), 6.32(1H,s), 6.41(1H,t), 7.06(2H,brs), 7.13(3H,d), 7.50 (3H,t), 7.60(3H,brs), 8.05(3H,brs), 9.67(1H,s)

Example 13

[3-(acridin-9-yl)amino-5-amino]benzyl N-(2-chlorophenyl) carbamate 3-(9-acridinylamino)-5-(hydroxymethyl)aniline and phenyl N-(2-chlorophenyl) carbamate were reacted with the same method to the example 1 to give the titled compound.

Yield: 42.0% m.p.: 162~164° C.

¹H NMR(DMSO-d₆): δ 5.03(2H,s), 6.34(4H,s), 6.97(1H, d), 7.12(2H,t), 7.29(2H,d), 7.55(2H,brs), 7.62(2H,s), 8.02 (2H,brs), 8.80(1H,s)

Example 14

[3-(acridin-9-yl)amino-5-amino]benzyl N-(3-chlorophenyl) carbamate 3-(9-acridinylamino)-5-(hydroxymethyl)aniline and phenyl N-(3-chlorophenyl) carbamate were reacted with the same method to the example 1 to give the titled compound.

Yield: 46.8% m.p.: 135~137° C.

¹H NMR(DMSO-d₆): δ 5.03(2H,s), 6.13(1H,s), 6.34(3H, s), 6.97(1H,d), 7.17(2H,t), 7.29(2H,d), 7.55(2H,brs), 7.62 (2H,s), 8.08(2H,brs), 8.80(1H,s)

Example 15

[3-(acridin-9-yl)amino-5-amino]benzyl N-(3,5-dichlorophenyl) carbamate 3-(9-acridinylamino)-5-(hydroxymethyl)aniline and phenyl N-(3,5-dichlorophenyl) carbamate were reacted with the same method to the example 1 to give the titled compound.

Yield: 44.2% m.p.: 188~190° C.

¹H NMR(DMSO-d₆): δ 5.06(2H,s), 6.68(1H,s), 6.93(1H, s), 7.16(2H,brs), 7.45(2H,s), 7.67(4H,brs), 7.94(2H,s), 8.13 (2H,brs), 8.82(1H,brs), 9.03(1H,brs)

Example 16

[3-(acridin-9-yl)amino-5-amino]benzyl N-(3-hydroxyphenyl) carbamate 3-(9-acridinylamino)-5-(hydroxymethyl)aniline and phenyl N-(3-hydroxyphenyl) carbamate were reacted with the same method to the example 1 to give the titled compound.

Yield: 37.8% m.p.: 152~153° C.

¹H NMR(DMSO-d₆): δ 4.98(1H,s), 5.08(2H,s), 6.27(1H, s), 6.42(1H,d), 6.88(1H,d), 7.06(4H,m), 7.31(2H,brs), 7.48 (4H,brs), 8.21(2H,brs), 9.35(1H,s), 9.61(1H,s), 10.82 (1H, brs)

Example 17

[3-(acridin-9-yl)amino-5-amino]benzyl N-(3-methoxyphenyl)thiocarbamate a) Phenyl N-(3-methoxyphenyl)thiocarbamate Triethylamine (0.87 g, 8.63 mmol) was added to a solution of 3-methoxyaniline (1 g, 8.63 mmol) dissolved in dichloromethane (20 ml), and thereto phenylchlorothioformate (1.49 g, 8.63 mmol) was added by dropping. The resulting solution was stirred for 2 hours at the room temperature, washed with distilled water, concentrated and purified by column chromatography to give the titled compound.

Yield: 77.4% m.p.: 166~168° C.

$^1$H NMR(CDCl$_3$): δ 5.11(1H,brs), 6.61(1H,dd), 6.64(2H, d), 7.11(3H,m), 7.20(2H,m), 7.35(2H,m)

b) [3-(acridin-9-yl) amino-5-amino]benzyl N-(3-methoxyphenyl)thiocarbamate 3-(9-acridinylamino)-5-(hydroxymethyl)aniline (0.75 g, 2.38 mmol) and phenyl N-(3-methoxyphenyl)thiocarbamate (0.62 g, 2.38 mmol) were dissolved in dimethylformaldehyde (40 ml), and thereto DBU (0.36 g, 2.38 mmol) was added by dropping. The resulting solution was stirred for 12 hours at the room temperature, and the solvent used was removed under the reduced pressure. Then, column chromatography was carried out to give the titled compound.

Yield: 59.4% m.p.: 163~165° C.

$^1$H NMR(DMSO-d$_6$): δ 3.76(3H,s), 5.01(2H,s), 6.66(2H, s), 6.95(2H,m), 7.10(1H,s), 7.17(1H,s), 7.22(1H,s), 7.52 (6H,brs), 8.00(2H,d), 9.39(1H,s), 9.55(1H,s), 10.8(1H,brs)

Example 18

[3-(acridin-9-yl)amino-5-amino]benzyl N-(3,5-dimethoxyphenyl)thiocarbamate 3-(9-acridinylamino)-5-(hydroxymethyl)aniline and phenyl N-(3,5-dimethoxyphenyl) thiocarbamate were reacted with the same method to the example 17 to give the titled compound.

Yield: 51.7% m.p.: 158~160° C.

$^1$H NMR(DMSO-d$_6$): δ 3.74(3H,s), 5.44(2H,s), 6.23(1H, s), 6.74(2H,s), 6.83(1H,s), 7.22(4H,m), 7.65(4H,m), 8.15 (2H,brs), 9.41(1H,brs), 9.55(1H,brs)

Example 19

[3-(acridin-9-yl)amino-5-amino]benzyl N-(3,4,5-trimethoxyphenyl)thiocarbamate 3-(9-acridinylamino)-5-(hydroxymethyl)aniline and phenyl N-(3,4,5-trimethoxyphenyl)thiocarbamate were reacted with the same method to the example 17 to give the titled compound.

Yield: 47.9% m.p.: 148~150° C.

$^1$H NMR(DMSO-d$_6$): δ 3.60(3H,s), 3.74(6H,s), 5.44(2H, s), 6.25(1H,s), 6.73(2H,s), 6.83(1H,s), 7.21(4H,m), 7.75 (4H,m), 8.15(2H,brs), 9.41(1H,brs), 9.55(1H,brs)

Example 20

3-(acridin-9-yl)aminobenzyl N-(3-methoxyphenyl) carbamate

[3-(9-acridinylamino)phenyl]methanol (1.37 g, 4.56 mmol) and phenyl N-(3-methoxyphenyl) carbamate (1.11 g, 4.56 mmol) were dissolved in dimethylformaldehyde (40 ml) and thereto DBU (0.69 g, 4.56 mmol) was added by dropping. The resulting mixture was stirred for 6 hours at the room temperature and the solvent used was removed under the reduced pressure. Then, the resulting product was purified by column chromatography to give the titled compound.

Yield; 70.4% m.p.: 77~78° C.

$^1$H NMR(DMSO-d$_6$): δ 3.78(3H,s), 5.12(2H,s), 6.16(1H, d), 6.84(3H,t), 7.00(2H,m), 7.11(1H,brs), 7.18(1H,t), 7.24 (2H,m), 7.58(2H,t), 7.92(2H,brs), 7.9?(2H,d)

Example 21

3-(acridin-9-yl)aminobenzyl N-(3,5-dimethoxyphenyl) carbamate 3-(9-acridinylamino)phenylmethanol and phenyl N-(3,5-dimethoxyphenyl) carbamate were reacted with the same method to the example 20 to give the titled compound.

Yield; 68.9% m.p.: 108~110° C.

$^1$H NMR(DMSO-d$_6$): δ 3.76(6H,s), 5.13(2H,s), 6.19(1H, s), 6.60(2H,s), 6.73(1H,brs), 6.8–6(1H,brs), 7.02(2H,m), 7.25(6H,brs), 7.59(2H,brs), 7.99(2H,brs)

Example 22

3-(acridin-9-yl)aminobenzyl N-(3,4,5-trimethoxyphenyl) carbamate 3-(9-acridinylamino)phenylmethanol and phenyl N-(3,4,5-trimethoxyphenyl) carbamate were reacted with the same method to the example 20 to give the titled compound.

Yield: 67.9% m.p.: 94~96° C.

$^1$H NMR(DMSO-d$_6$): δ 3.59(3H,s), 3.70(6H,s), 5.12(2H, s), 6.69(2H,d), 6.83(3H,d), 7.01(2H,d), 7.32(3H,m), 7.45 (2H,brs), 8.11(1H,brs), 9.64(1H,brs), 10.90(1H,s)

Example 23

[3-(3,4-dimethylacridin-9-yl)amino-5-amino]benzyl N-(3,5-difluorophenyl) carbamate 3-(3,4-dimethylacridin-9-yl) amino-5-(hydroxymethyl) aniline and phenyl N-(3,5-difluorophenyl) carbamate were reacted with the same method to the example 1 to give the titled compound.

Yield: 51.6% m.p.: 190~191° C.

$^1$H NMR(DMSO-d$_6$): δ 2.49(3H,s), 2.83(3H,s), 5.02(2H, s), 5.13(1H,s), 5.81(1H,s), 6.15(2H,d), 6.88(2H,m), 7.18 (1H,m), 7.30(1H,d), 7.45(1H,m), 7.73(1H,m), 7.94(1H,d) 8.11(1H,d), 8.16(1H,d), 8.85(1H,s), 10.17(1H,s)

Example 24

[3-(3,4-dimethylacridin-9-yl)amino-5-amino]benzyl N-(3,5-dichlorophenyl) carbamate 3-(3,4-dimethylacridin-9-yl)amino-5-(hydroxymethyl) aniline and phenyl N-(3,5-dichlorophenyl) carbamate were reacted with the same method to the example 1 to give the titled compound.

Yield: 52.5% m.p.: 136~138° C.

$^1$H NMR(DMSO-d$_6$): δ 2.47(3H,s), 2.81(3H,s), 4.97(2H, s), 5.06(1H,s), 5.92(1H,s), 6.14(2H,m), 7.24(2H,m), 7.42 (1H,m), 7.53(2H,s), 7.71(1H,m), 7.94(1H,m), 8.15(2H,m), 8.88(1H,s), 10.16(1H,s)

Example 25

[3-(2-methylacridin-9-yl)amino-5-amino]benzyl N-(3,5-dichlorophenyl) carbamate 3-(2-methylacridin-9-yl)amino-5-(hydroxymethyl)aniline and phenyl N-(3,5-dichlorophenyl) carbamate were reacted with the same method to the example 1 to give the titled compound.

Yield: 53.7% m.p.: 208~209° C.

$^1$H NMR(DMSO-d$_6$): δ 2.35(3H,s), 5.01(2H,s), 5.15(1H, s), 6.02(1H,s), 6.14(1H,s), 6.29(1H,s), 7.25(2H, ), 7.53(4H, m), 7.61(2H,m), 7.96(2H,m), 10.16(1H,s)

Example 26
[3-(2-methylacridin-9-yl)amino-5-amino]benzyl N-(3,5-difluorophenyl) carbamate 3-(2-methylacridin-9-yl)amino-5-(hydroxymethyl)aniline and phenyl N-(3,5-difluorophenyl) carbamate were reacted with the same method to the example 1 to give the titled compound.

Yield; 56.5%
m.p.: 170~172° C.
$^1$H NMR(DMSO-d$_6$): δ 2.37(3H,s), 5.03(2H,s), 5.18(1H, s), 6.14(1H,s), 6.24(1H,s), 6.37(1H,s), 6.88(2H,m), 7.17 (4H,m), 7.68(2H,m), 8.03(2H,m), 10.19(1H,s)

Example 27
[3-(2,3-dimethylacridin-9-yl)amino-5-amino]benzyl N-(3,5-difluorophenyl) carbamate 3-(2, 3-dimethylacridin-9-yl) amino-5-(hydroxymethyl) aniline and phenyl N-(3,5-difluorophenyl) carbamate were reacted with the same method to the example 1 to give the titled compound.

Yield: 51.2%
m.p.: 140~142° C.
$^1$H NMR(DMSC-d$_6$): δ 2.25(3H,s), 2.39(3H,s), 5.02(2H, s), 5.18(1H,s), 6.07(1H,s), 6.19(1H,s), 6.33(1H,s), 6.87(1H, m), 7.17(3H,m), 7.65(4H,m), 8.05(1H,m), 10.18(1H,s)

Example 28
[3-(4-methoxyacridin-9-yl)amino-5-amino]benzyl N-(3,5-difluorophenyl) carbamate 3-(4-methoxyacridin-9-yl)amino-5-(hydroxymethyl) aniline and phenyl N-(3,5-difluorophenyl) carbamate were reacted with the same method to the example 1 to give the titled compound.

Yield: 57.5%
m.p.: 178~180° C.
$^1$H NMR(DMSO-d$_6$): δ 4.03(3H,s), 5.01(2H,s), 5.10(1H, s), 5.96(1H,s), 6.07(1H,s), 6.26(1H,s), 6.87(1H,m), 7.19 (4H,m), 7.50(2H,m), 7.75(2H,m), 8.15(1H,m), 10.21(1H,s), 10.27(1H,s)

Example 29
[3-(4-methoxyacridin-9-yl)amino-5-amino]benzyl N-(3,5-dichlorophenyl) carbamate 3-(4-methoxyacridin-9-yl) amino-5-(hydroxymethyl) aniline and phenyl N-(3,5-dichlorophenyl) carbamate were reacted with the same method to the example 1 to give the titled compound.

Yield: 58.6%
m.p.: 230~232° C.
$^1$H NMR(DMSO-d$_6$): δ 4.02(3H,s), 5.02(2H,s), 5.09(1H, s), 5.95(1H,s), 6.03(1H,s), 6.26(1H,s), 7.11(2H,m), 7.24(1H, s), 7.54(4H,m), 7.72(2H,m), 8.16(1H,m), 10.18(1H,s), 10.24 (1H,s)

Example 30
N-[3-(acridin-9-yl)amino-5-hydroxymethyl]phenyl N'-(3,5-difluorophenyl)urea a) Phenyl N-(3,5-difluorophenyl) carbamate Triethylamine (1.11 g, 11.0 mmol) was added to a solution of 3,5-difluoroaniline (1.42 g, 11.0 mmol) dissolved in dichloromethane (20 ml), and thereto phenylchloroformate 1.76 g, 11.2 mmol) was added by dropping. The resulting mixture was stirred for 2 hours at the room temperature, washed with distilled water, concentrated and purified by column chromatography to give the titled compound.

Yield; 86.5%
m.p.: 126~128° C.
$^1$H NMR(CDCl$_3$): δ 6.84(3H,s), 7.30(5H,d)

b) N-[3-(acridin-9-yl)amino-5-hydroxymethyl]phenyl N'-(3,5-difluorophenyl)urea 3-(9-acridinylamino)-5-(hydroxymethyl)aniline (1.00 g, 3.17 mmol) and phenyl N-(3,5-difluorophenyl) carbamate (0.79 g, 3.17 mmol) were dissolved in dimethylformaldehyde (40 ml), and thereto DBU (0.48 g, 3.17 mmol) was added by dropping. The resulting solution was stirred for 2 hours at the room temperature and the solvent used was removed under the reduced pressure. Then, purification by column chromatography was carried out to give the titled compound.

Yield: 21.0%
m.p.: 125~128° C.
$^1$H NMR(DMSO-d$_6$): δ 4.70(2H,s), 5.04(2H,s), 6.36(1H, s), 6.41(2H,m), 6.54(1H,s), 7.13(2H,d), 7.20(2H,brs), 7.67 (2H,brs), 7.74(2H,brs), 8.18(2H,brs), 9.79(1H,s)

Example 31
N-[3-(acridin-9-yl)amino-5-hydroxymethyl]phenyl N'-(3-fluorophenyl) urea 3-(9-acridinylamino) -5-(hydroxymethyl) aniline and phenyl N-(3-fluorophenyl) carbamate were reacted with the same method to the example 30 to give the titled compound.

Yield: 20.2%
m.p.: 292° C. (decomposed)
$^1$H NMR(DMSO-d$_6$): δ 4.57(2H,s), 7.24(1H,s), 7.27(2H, d), 7.47(2H,m), 7.85(5.H,s), 8.00(2H,m), 8.21(2H,d), 8.37 (2H,d), 11.5(1H,s)

Example 32
N-[3-(acridin-9-yl)amino-5-hydroxymethyl]phenyl N'-(3,5-dichlorophenyl) urea 3-(9-acridinylamino)-5-(hydroxymethyl)aniline and phenyl N-(3,5-dichlorophenyl) carbamate were reacted with the same method to the example 30 to give the titled compound.

Yield: 18.5%
m.p.: 180~181° C.
$^1$H NMR(DMSO-d$_6$): δ 4.52(2H,s), 5.06(1H,s), 6.68(1H, s), 6.93(1H,s), 7.18 (3H,m), 7.45(2H,s), 7.67(4H,m) 7.94 (2H,s) 8.13(2H,m), 8.82(1H,s), 9.03(1H,s)

Example 33
N-[3-(4-methoxyacridin-9-yl)amino-5-hydroxymethyl] phenyl N'-(3,5-difluorophenyl)urea 3-(4-methoxyacridin-9-yl)amino-5-(hydroxymethyl) aniline and phenyl N-(3,5-difluorophenyl) carbamate were reacted with the same method to the example 30 to give the titled compound.

Yield: 20.5%
m.p.: 164~165° C.
$^1$H NMR(DMSO-d$_6$): δ 4.03(3H,s), 4.52(2H,s), 6.36(1H, s), 6.78(2H,m), 7.03(3H,m), 7.11(2H,m), 7.13(4H,m), 8.19 (2H,m), 8.69(1H,s), 10.93(1H,s)

Example 34
N-[3-(3,4-dimethylacridin-9-yl)amino-5-hydroxymethyl] phenyl N'-(3, 5-difluorophenyl)urea 3-(9-acridinylamino)-5-(hydroxymethyl)aniline and phenyl N-(3,5-difluorophenyl) carbamate were reacted with the same method to the example 30 to give the titled compound.

Yield: 20.2%
m.p.: 185~186° C.
$^1$H NMR(DMSO-d$_6$): δ 2.49(2H,s), 2.84(3H,s), 4.37(2H, s), 5.11(1H,s), 6.47(1H,s), 6.70(1H,s), 6.79(1H,m), 7.01(1H, s), 7.15(2H,m), 7.35(1H,m), 7.48(1H,m), 7.79(1H,m), 7.95 (1H,m), 8.16(2H,m), 8.71(1H,s), 8.96(1H,s), 9.06(1H,s)

Example 35
3-(acridin-9-yl)amino-5-(ethylideneamino)phenylmethanol 3-(9-acridinylamino)-5-(hydroxymethyl)aniline was dissolved in dichloromethane/pyridine(1/1, v/v, 40 ml), and thereto acetaldehyde (2.09 g, 47.56 mmol) was added. The resulting mixture was stirred for 5 hours, and the solvent used was removed under the reduced pressure. Then, the resulting product was purified by column chromatography to give the titled compound.

Yield: 80.1%
m.p.: 158~161° C.
$^1$H NMR(DMSO-d$_6$): δ 2.63(3H,s), 5.00(2H,s), 5.16(1H, brs), 7.11(2H,d), 7.17(1H,d), 7.35(1H,s), 7.60(2H,brs), 7.76 (4H,brs), 8.10(2H,brs), 8.30(1H,d)

Example 36
3-(acridin-9-yl)amino-5-(propylideneamino)phenylmethanol 3-(9-acridinylamino)-5-(hydroxymethyl)aniline and propylaldehyde were reacted with the same method to the example 35 to give the titled compound.

Yield: 78.9%
m.p.: 262~263° C.
$^1$H NMR(DMSO-d$_6$): δ 1.28(3H,t), 2.88(2H,m), 4.98(2H, s), 5.06(1H,brs), 5.42(1H,s), 7.09(3H,s), 7.28(1H,s), 7.56 (3H,s), 7.73(1H,s), 8.80(3H,s)

Example 37
3-(acridin-9-yl)amino-5-(butylideneamino)phenylmethanol 3-(9-acridinylamino) -5-(hydroxymethyl) aniline and butylaldehyde were reacted with the same method to the example 35 to give the titled compound.

Yield: 77.5%
m.p.: 228~230° C.
$^1$H NMR(DMSO-d$_6$): δ 1.25(3H,t), 2.44(2H,s), 2.86(2H, m), 4.90(2H,d), 5.35(1H,s), 7.00(2H,d), 7.33(2H,d), 7.48 (3H,brs), 7.82(1H,brs), 7.98(2H,brs), 8.08(1H,brs), 8.18 (1H,brs), 9.43(1H,s), 10.97(1H,s)

Example 38
t-butyl N-{2-[3-(acridin-9-yl)amino-5-(hydroxymethyl)anilino]-2-oxoethyl}carbamate 3-(9-acridinylamino) -5-(hydroxymethyl) aniline (1.00 g, 3.17 mmol) was dissolved in pyridine (30 ml), and thereto WSCD (0.62 g, 3.17 mmol), HOBT (0.43 g, 3.17 mmol) and 2-[(t-butoxycarbonyl)amino]acetic acid (0.56 g, 3.17 mmol) were added. The resulting solution was stirred for 10 hours at 0° C., and the solvent used was removed under the reduced pressure. Then, the resulting product was purified by column chromatography to give the titled compound.

Yield: 78.8%
m.p.: 193~195° C.
$^1$H NMR(DMS(-d$_6$): δ 1.43(9H,s), 3.81(2H,s), 4.54(2H, s), 5.13(1H,s), 6.56(1H,s), 6.85(1H,s), 7.27(2H,s), 7.37–7.54(2H,m), 7.64(1H,d), 7.98(2H,brs), 7.78(1H,s), 7.79(2H,s), 8.19(1H,s), 9.87(1H,s)

Example 39
t-butyl N-{2-[3-(acridin-9-yl)amino-5-(hydroxymethyl)anilino]-1-methyl-2-oxoethyl}carbamate 3-(9-acridinylamino)-5-(hydroxymethyl)aniline and t-butoxycarbonyl-L-alanine were reacted with the same method to the example 38 to give the titled compound.

Yield: 77.2%
m.p.: 131~133° C.
$^1$H NMR(DMSO-d$_6$): δ 1.33(3H,d), 1.42(9H,s), 4.23(1H, m), 4.53(2H,d), 5.09(1H,brs), 6.41(1H,d), 6.81(1H,brs), 7.27(2H,brs), 7.42(1H,s), 7.76(2H,brs), 7.84(1H,brs), 8.19 (1H,brs), 9.83(1H,brs)

Example 40
t-butyl N-{2-[3-(acridin-9-yl)amino-5-(hydroxymethyl)anilino]-(2S)-1-benzyl-2-oxoethyl}carbamate 3-(9-acridinylamino)-5-(hydroxymethyl)aniline and t-butoxycarbonyl-L-phenylalanine were reacted with the same method to the example 38 to give the titled compound.

Yield; 68.7%
m.p.: 193~195° C.
$^1$H NMR(DMSO-d$_6$): δ 1.35(9H,s), 2.89(2H,m), 3.09(1H, m), 4.51(2H,s), 6.01(1H,s), 7.02(1H,s), 7.07(1H,brs), 7.16 (1H,brs), 7.22(5H,s), 7.28(1H,s), 7.54(2H,m), 7.59(1H,brs), 8.03(2H,brs), 9.63(1H,s)

Example 41
t-butyl N-{2-[3-(acridin-9-yl)amino-5-(hydroxymethyl)anilino]-(2S)-1-isopropyl-2-oxoethyl}carbamate 3-(9-acridinylamino)-5-(hydroxymethyl)aniline and t-butoxycarbonyl-L-valine were reacted with the same method to the example 38 to give the titled compound.

Yield: 72.8%
m.p.: 179~180° C.
$^1$H NMR(DMSO-d$_6$): δ 1.32(6H,t), 1.42(9H,s), 2.36(1H, m), 4.01(1H,d), 4.74(2H,s), 7.29(1H,s), 7.46(2H,t) r 7.63 (1H,s), 7.76(1H,s), 7.78(4H,m), 8.23(2H,d)

Example 42
t-butyl N-{2-[3-(acridin-9-yl)amino-5-(hydroxymethyl)anilino]-(2S)-1-(2-isobutyl)-2-oxoethyl}carbamate 3-(9-acridinylamino)-5-(hydroxymethyl)aniline and t-butoxycarbonyl-L-leucine were reacted with the same method to the example 38 to give the titled compound.

Yield: 68.7%
m.p.: 262~263° C.
$^1$H NMR(DMSO-d$_6$): δ 0.94(6H,t), 1.42(2H,m), 1.46(9H, s), 1.75(1H,m), 3.35(1H,m), 4.73(2H,s), 7.19(1H,s), 7.47 (2H,t), 7.74(1H,s), 7.85(1H,s), 7.80(4H,m), 8.35(2H,d)

Example 43
t-butyl N-{2-[3-(acridin-9-yl)amino-5-(hydroxymethyl)anilino]-(2S)-1-sec-butyl-2-oxoethyl) carbamate 3-(9-acridinylamino)-5-(hydroxymethyl)aniline and t-butoxycarbonyl-L-isoleucine were reacted with the same method to the example 38 to give the titled compound.

Yield; 61.9%
m.p.: 280~282° C.
$^1$H NMR(DMSO-d$_6$): δ 0.90(3H,t), 0.96(3H,d), 1.29(2H, m), 1.43(9H,s), 1.98(1H,m), 3.40(1H,d), 4.73(2H,s), 7.29 (1H,s), 7.56(2H,t), 7.74(1H,s), 7.85(1H,s), 7.90(4H,m), 8.25 (2H,d)

Example 44
N-[3-(acridin-9-yl)amino-5-(hydroxymethyl)phenyl]aminoethaneamide Anisole (0.47 g, 4.28 mmol) and acetonitrile/dichloromethane (1/2, v/v, 25 ml) were added to t-butyl N-{2-[3-(9-acridinylamino)-5-(hydroxymethyl)anilino]-2-oxoethyl}carbamate (0.34 g, 0.71 mmol). To the resulting mixture, aluminium chloride (0.57 g, 4.28 mmol) was slowly added with stirring and stirred for 2 hours at the room temperature. The resulting product was concentrated under the reduced pressure and purified by column chromatography to give the titled compound.

Yield: 62.7%
m.p.: 360° C. (decomposed)

¹H NMR(DMSO-d₆): δ 3.87(2H,s), 4.63(2H,s), 7.19(1H, s), 7.45(2H,m), 7.64(1H,s), 7.72(1H,s), 7.99(4H,d), 8.24 (2H,d)

Example 45
N-[3-(acridin-9-yl)amino-5-(hydroxymethyl)phenyl](2S)-2-aminopropaneamide The same reaction procedure to the example 44 was carried out using t-butyl N-{2-[3-(9-acridinylamino)-5-(hydroxymethyl) anilino]-1-methyl-2-oxoethyl}carbamate to give the titled compound.

Yield: 59.6%
m.p.; 289~291° C.
¹H NMR(DMSO-d₆): δ 1.57(3H,d), 4.09(1H,q), 4.63(2H, s), 7.19(1H,s), 7.46(2H,t), 7.64(1H,s), 7.75(1H,s), 7.99(4H, m), 5 8.23(2H,d)

Example 46
N-[3-(acridin-9-yl)amino-5-(hydroxymethyl)phenyl](2S)-2-amino-3-phenylpropaneamide The same reaction procedure to the example 44 was carried out using t-butyl N-12-[3-(9-acridinylamino)-5-(hydroxymethyl)anilino]-1-benzyl-2-oxoethyl}carbamate to give the titled compound.

Yield: 54.9%
m.p.: 246~249° C.
¹H NMR(DMSO-d₆): δ 2.89(2H,m), 3.09(1H,m), 4.51 (2H,s), 6.01(1H,s), 7.02(1H,s), 7.07(1H,brs), 7.16(1H,brs), 7.25(5H,s), 7.28(1H,s), 7.54(2H,m), 7.59(1H,brs), 8.03(2H, brs), 9.63(1H,s)

Example 47
N-[3-(acridin-9-yl)amino-5-(hydroxymethyl)phenyl](2S)-2-amino-3-methylbutaneamide The same reaction procedure to the example 44 was carried out using t-butyl N-{2-[3-(9-acridinylamino)-5-(hydroxymethyl)anilino]-1-isopropyl-2-oxoethyl}carbamate to give the titled compound.

Yield: 53.7%
m.p.:181~183° C.
¹H NMR(DMSO-d₆): δ 0.99(6H,s), 2.16(1H,m), 3.74(1H, s), 4.48(2H,s), 5.23(1H,s), 6.53(1H,s), 7.00(2H,m), 7.21 (1H,m), 7.38(2H,m), 7.52(2H,m), 8.15(4H,m), 10.45(1H,s), 11.03(1H,s)

Example 48
N-[3-(acridin-9-yl)amino-5-(hydroxymethyl)phenyl](2S)-2-amino-4-methylpentaneamide The same reaction procedure to the example 44 was carried out using t-butyl N-{2-[3-(9-acridinylamino)-5-(hydroxymethyl)anilino]-1-(2-isobutyl)-2-oxoethyl}carbamate to give the titled compound.

Yield: 48.5%
m.p.; 220~223° C.
¹H NMR(DMSO-d₆): δ 0.96(6H,d), 1.69(3H,m), 4.04 (1H,s), 4.51(2H,s), 5.41(1H,s), 7.00(1H,s), 7.50(4H,m), 7.96(4H,m), 8.26(1H,m), 8.39(2H,m), 10.98(1H,s)

Example 49
N-[3-(acridin-9-yl)amino-5-(hydroxymethyl)phenyl](2S)-2-amino-3-methylpentaneamide The same reaction procedure to the example 44 was carried out using t-butyl N-{2-[3-(9-acridinylamino)-5-(hydroxymethyl)anilino]-1-sec-butyl-2-oxoethyl}carbamate to give the titled compound.

Yield: 46.8%
m.p.: 177~179° C.
¹H NMR(DMSO-d₆): δ 0.90(3H,m), 0.96(3H,m), 1.18 (1H,m), 1.59(1H,m), 1.90(1H,m), 3.73(1H,s), 4.49(1H,s), 5.24(1H,s), 6.52(1H,s), 7.13(2H,m), 7.36(2H,m), 7.51(2H, m), 8.17 (4H,m), 10.34(1H,s), 10.99(1H,s)

Example 50
N-[3-(2-methylacridin-9-yl)amino-5-(hydroxymethyl)phenyl](2S)-2-aminopropaneamide The same reaction procedure to the example 44 was carried out using t-butyl N-{2-[3-(2-methylacridin-9-yl)amino-5-(hydroxymethyl)anilino]-1-methyl-2-oxoethyl}carbamate to give the titled compound.

Yield: 61.5%
m.p.: 280° C. (decomposed)
¹H NMR(DMSO-d₆): δ 1.50(3H,d), 2.45(3H,s), 4.16(1H, s), 4.49(2H,s), 5.44(1H,s), 7.05(1H,s), 7.41(1H,m), 7.65(!H, s), 7.72(1H,s), 7.97(2H,m), 8.18(2H,m), 8.33(1H,s), 8.44 (2H,s), 11.21 (1H,brs)

Example 51
N-[3-(3,4-dimethylacridin-9-yl) amino-5-(hydroxymethyl)phenyl](2S)-2-aminopropaneamide The same reaction procedure to the example 44 was carried out using t-butyl N-{2-[3-(3,4-dimethylacridin-9-yl)amino-5-(hydroxymethyl)anilino]-1-methyl-2-oxoethyl}carbamate to give the titled compound.

Yield: 62.4%
m.p.: 238~240° C.
¹H NMR(DMSO-d₆): δ 1.47(3H,d), 2.52(3H,s), 2.76(3H, s), 4.11(1H,s), 4.45(2H,s), 5.37(1H,s), 6.90(1H,s), 7.33(1H, m), 7.44(2H,m), 7.92(1H,s), 8.01(1H,s), 8.26(1H,s), 8.43 (3H,m), 11.21(1H,brs)

Example 52
N-[3-(4-methoxyacridin-9-yl)amino-5-(hydroxymethyl)phenyl](2S)-2-aminopropaneamide The same reaction procedure to the example 44 was carried out using t-butyl N-{2-[3-(4-methoxyacridin-9-yl)amino-5-(hydroxymethyl)anilino]-1-methyl-2-oxoethyl}carbamate to give the titled compound.

Yield: 60.2%
m.p.: 260° C. (decomposed)
¹H NMR(DMSO-d₆): δ 1.51(3H,d), 3.19(1H,s), 4.19(3H, s), 4.48(2H,s), 7.06 (1H,s), 7.42 (1H,m), 7.43 (1H,m), 7.58(1H, d), 7.75(2H,d), 7.93(1H,d), 8.01(1H,m), 8.38(1H, d), 8.47(1H,d), 8.55(1H,s), 11.44(1H,brs)

Example 53
N-[3-(acridin-9-yl)amino-5-(hydroxymethyl)phenyl](2S)-2-amino-6-aminohexaneamide The same reaction procedure to the example 44 was carried out using t-butyl N-(2-[3-(acridin-9-yl)amino-5-(hydroxymethyl) anilino]-1-methyl-2-oxoethyl carbamate to give the titled compound.

Yield: 48.5%
m.p.: 281° C. (decomposed)
¹H NMR(DMSO-d₆): δ 1.47(2H,m), 1.65(2H,m), 1.89 (2H,m), 2.77(2H,m), 4.14(2H,m), 4.48(2H,s), 5.42(1H,s), 6.97(1H,m), 7.41(2H,m), 7.60(2H,m), 7.93(2H,m), 8.20 (4H,m), 8.56(2H,s), 11.32(1H,s)

The compounds prepared in the examples according to the present invention were tested for pharmacological activities against tumors. Antitumor activities of the compounds were tested in vitro against 5 kinds of human tumor cell lines and 2 kinds of leukemia tumor cell lines. In addition, inhibition effects of the compounds against the DNA Topoisomerase were measured by using DNA relaxation assay and DNA cleavage assay. Methods and results of the tests are as follows.

Experimental 1

In vitro antitumor effect against human tumor cell lines.

A. Tumor cell lines: A549 (human non-small lung cell)

SKOV-3 (human ovarian)

HCT-15 (human colon)

XF-498 (human CNS)

SKMEL-2 (human melanoma)

B. Method: SRB Assay a. Human solid tumor cell lines, A549(non-small lung cell), SKMEL-2(melanoma), HCT-15(colon), SKOV-3 (ovarian) and XF-498(CNS) were cultured in 5% CO, incubators using the RPMI 1640 media containing 10% FBS at 37° C., while with transfer-culturing successively once or twice per week. Cell cultures were dissolved in a solution of 0.25% trysin and 3 mmol CDTA PBS(−) to separate the cells sticked on the culture media.

b. $5 \times 10^3 \sim 2 \times 10^4$ cells were added into each well of 96-well plate and cultured in 5% CO, incubator at 37° C. for 24 hours.

c. Each sample drug was dissolved in a little DMSO and diluted with the used medium to a prescribed concentration for experiment, while the final concentration of DMSO was adjusted below 0.5%.

d. Medium of each well cultured for 24 hours as above b. was removed by aspiration. Each 200 μl of drug samples prepared in c. was added into each well and tine wells were cultured for 48 hours. Tz (time zero) plates were collected at the point of time drugs were added.

e. According to the SRB assay method, cell fixing with TCA, staining with 0.4% SRB solution, washing with 1% acetic acid and elution of dye with 10 mmol Tris solution were carried out on Tz plates and culture-ended plates, and then, OD values were measured at 520 nm.

C. Calculation of Result a. Time zero (Tz) value was determined with measuring the SRB protein value at the point of time drugs were added.

b. Control value (C) was determined with the OD value of an well untreated with drug.

c. Drug-treated test value (T) was determined with the OD value of drug-treated well.

d. Effects of drugs were estimated with growth stimulation, net growth inhibition and net killing calculated from Tz, C and T values.

e. If $T \geq Tz$, cellular response function was calculated by $100 \times (T-Tz)/(C-Tz)$, and, if $T \leq Tz$, by $100 \times (T-Tz)/Tz$. The results are shown in the next table 1.

REFERENCE

1) P. Skehan, R. Strong, D Scudiero, A. Monks, J. B. Mcmahan, D. T. Vistica, J. Warren, H. Bokesh, S. Kenney and M. R. Boyd: Proc. Am. Assoc. Cancer Res., 30, 612 (1989).

2) L. V. Rubinstein, R. H. Shoemaker, K. D. Paull, R. M. Simon, S. Tosini, P. Skehar, D. Scudiero, A. Monks and M. R. Boyd; J. Natl. Cancer Inst., 82, 1113 (1990).

P. Skehan, R. Strong, D. Scudiero, A. Monks, J. B. Mcmahan, D. T. Vistica, J. Warren, H. Bokesch, S. Kenney and M. R. Boyd. J, Natl. Cancer Inst., 82, 1107 (1990).

D. Results

It was found that the compounds of the present invention have the even or superior antitumor activities than that of cisplatin, the control against human solid cancer cell lines.

TABLE 1

| Comp. (No. of ex.) | A 549 | SK-OV-3 | SK-MEL-2 | XF-498 | HCT 15 |
|---|---|---|---|---|---|
| 1 | 0.96 | 1.15 | 0.49 | 0.44 | 0.57 |
| 2 | 1.12 | 0.68 | 1.08 | 0.71 | 0.97 |
| 4 | 0.19 | 0.19 | 0.20 | 0.23 | 0.24 |
| 6 | 0.72 | 0.36 | 0.40 | 0.37 | 0.33 |
| 37 | 0.90 | 0.93 | 0.89 | 0.36 | 0.35 |
| 45 | 0.01 | 0.21 | 0.25 | 0.88 | 0.86 |
| Cisplatin | 0.81 | 0.71 | 0.71 | 0.77 | 3.03 |

$ED_{50} = \mu g/ml$

Experimental 2

In vitro antitumor effects against animal leukemia cells.

A. Material:

Tumor cell lines: P388 (mouse lymphoid neoplasma cell)

B. Method: Dye Exclusion Assay.

1) The concentration of P388 cells being cultured in RPMI 1640 media containing 10% FBS was adjusted to $1 \times 10^6$ cells/ml.

2) Each sample drug of a concentration diluted in the ratio of log dose was added into cell culture media and cultured at 37° C. for 48 hours in 50% $CO_2$ incubator, and then viable cell number was measured by dye exclusion test using trypan blue.

3) The concentration of each sample compound showing 50% cell growth inhibition ($IC_{50}$) compared with the control was determined and listed in the table 2 below.

REFERENCE

1) P. Skehan, R. Strong, D. Scudiero, A. Monks, J. B. Mcmahan, D. T. Vistica, J. Warren, H. Bokesch, S. Kenney and M. R. Boyd.: Proc. Am. Assoc. Cancer Res., 30, 612 (1989).

2) L. V. Rubinstein, R. H. Shoemaker, K. D. Paull, R. M. Simon, S. Tosini, P. Skehan, D. Scudiero, A. Monks and M. R. Boyd.: J. Natl. Cancer Inst., 82, 1113 (1990)

3) P. Skehan, R. Strong, D. Scudiero, J. B. Mcmahan, D. T. Vistica, J. Warren, H. Bokesch, S. Kenneyand M. R. Boyd.: J. Natl. Cancer Inst., 82, 1107(1990)

C. Results

As the result of measurement of antitumor activities against P388 mouse cancer cells of the compounds according to the present invention, it was found that the compounds tested have equal to or higher antitumor activities than those of the control drug, mitomycin C.

TABLE 2

| Comp. (No. of example) | P388 |
|---|---|
| 1 | 0.9 |
| 3 | 1.1 |
| 6 | 0.8 |
| 12 | 1.2 |
| 14 | 1.0 |
| 17 | 1.0 |
| 18 | 0.7 |
| 44 | 0.1 |
| 45 | 0.05 |
| 46 | 0.1 |
| MitomycinC | 1.1 |

Experimental 3:

Inhibition effects against the Topoisomerase II activities a) DNA relaxation assay.

The present compounds were tested for inhibition of Topoisomerase II activity by means of the relaxation assay using supercoiled pBR322 DNA as the substrate. Topo II and a sample inhibitor were added to a reaction system (50 mmol Tris-HCl, pH 7.5, 50 mmol KCl, 20 mmol $MgCl_2$, 0.5 mmol EDTA, 2 mmol ATP, 60 μg/ml BSA) containing supercoiled pBR322 DNA and reacted for 30 minutes at 37° C. Then, a quarter by volume of Stop buffer (5% SDS, 50 mmol EDTA, 30% glycerol, 0.1 mg/ml xylene cyanol, 0.1 mg/ml BPB) was added to the reaction system to stop the reaction. The resulting product went through electrophoresis on 0.7% agarose gel and was stained by ethidium bromide solution. Mobility of DNA was measured under ultraviolet rays.

b) DNA cleavage assay

Topo II and a sample inhibitor were added to cleavage buffer (30 mmol Tris-HCl, pH 7.5, 60 mmol KCl, 10 mmol $MgCl_2$, 15 mmol β-mercaptoethanol, 30 μg/ml BSA) containing supercoiled pBR322 DNA and allowed to react for 30 minutes at 37° C. Then, SDA by 1% was added to the reaction system to stop the reaction. Then, proteinase K was added thereto up to the concentration of 50 μg/ml and allowed to react for 30 minutes at 56° C. The reaction product was treated with phenol/chloroform to purify DNA, and the obtained DNA was loaded on agarose gel electrophoresis, transferred to nitrocellulose membrane and hybridized with probe DNA labelled with radioisotope. Then, the nitrocellulose membrane was covered with an X-ray film and exposed to be sensitized and developed, whereby the degree of cleavage of DNA was measured.

c) Results

As the result of inhibition tests against Topoisomerase II activity as shown in the following table, it was found that the compounds according to the present invention have the superior antitumor activity than the control, etoposide.

TABLE 3

| Comp. (No. of | $IC_{50}$ (μg/ml) | Comp. (No. of | $IC_{50}$ (μg/ml) |
|---|---|---|---|
| 1 | 1 | 21 | 3 |
| 2 | 3 | 22 | 5 |
| 3 | 3 | 35 | 5 |
| 4 | 5 | 36 | 3 |
| 6 | 3 | 37 | 5 |
| 12 | 0.5 | 44 | 3 |
| 14 | 1 | 45 | 0.5 |
| 18 | 3 | 46 | 3 |
| 19 | 5 | Etoposide | 10 |
| 20 | 3 | | |

Experimental 4

Acute Toxicity Test ($LD_{50}$):

a) Method: Litchfield-Wilcoxon Method.

6-week-old ICR mice(male 30±2.0 g) were fed freely with solid feed and water at room temperature, 23±1° C. and at humidity 60±5%. Sample drugs were injected into the abdominal cavities of mice. Each group comprised 6 mice. Observed during 14 days, external appearances and life or death thereof were recorded, and also, visible lesions were observed from dead mice by dissection. $LD_{50}$ value was calculated by Litchfield-wilcoxon method.

b) Results

As shown in the following table, the compounds according to the present invention are predominantly safe in comparison with cisplatin, whereby much problems of known compounds such as restriction of dosage, unfavorable side effects by toxicity, etc. may be overcome considerably.

TABLE 4

| Comp. | $LD_{50}$ (mg/kg) | |
|---|---|---|
| (No. of example) | i.p. | i.v. |
| 12 | 150 | |
| 45 | 730 | 133 |
| Cisplatin | 9.7 | |

As described above, the compounds according to the present invention are much more safer and also have much superior antitumor activities to known anticancer drugs, and accordingly the compounds are expected to be useful as a new anticancer agent.

What is claimed:

1. A compound of the general formula (I)

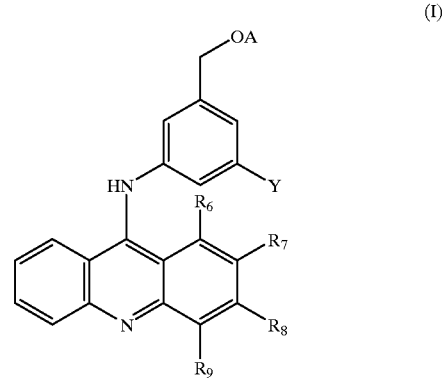

(I)

wherein A is hydrogen or

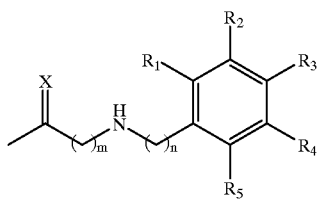

(wherein X is oxygen or sulfur, $R_1$, $R_2$, $R_3$, $R_4$ and $R_5$ are independently hydrogen, halogen, nitro, amino, hydroxy, $C_1$–$C_4$ lower alkylhydroxy, $C_1$–$C_4$ lower alkylamino, $C_1$–$C_8$ alkyl, $C_1$–$C_4$ lower alkoxy or $C_1$–$C_4$ lower alkyloxycarbonyl and m and n are independently an integer of 0, 1 or 2), $R_6$, $R_7$, $R_8$ and $R_9$ are independently $C_1$–$C_8$ alkyl or $C_1$–$C_4$ lower alkoxy, and Y is hydrogen, amino, —N═CHR' (wherein R' is hydrogen, benzyl, $C_1$–$C_8$ alkyl or $C_1$–$C_6$ lower alkylamino),

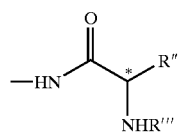

(wherein R'' is hydrogen, benzyl, $C_1$–$C_8$ alkyl or $C_1$–$C_6$ lower alkylamino, and R''' is hydrogen, benzyl, $C_1$–$C_8$ alkyl or amino protecting group) or

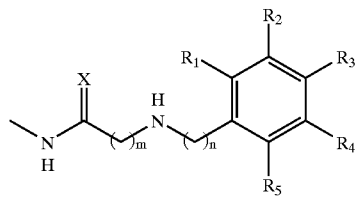

wherein, X is as defined above, $R_1'$, $R_2'$, $R_3'$, $R_4'$ and $R_5'$ are independently hydrogen, halogen, nitro, amino, hydroxy, $C_1$–$C_4$ lower alkylhydroxy, $C_1$–$C_4$ lower alkylamino, $C_1$–$C_8$ alkyl, $C_1$–$C_4$ lower alkoxy or $C_1$–$C_4$ lower alkylcarboxy, and m and n are independently an integer of 0, 1 or 2) or its pharmaceutically acceptable salt, wherein A and Y are not H at the same time, and when Y is amino group, A is not H.

2. A process for the preparation of a compound of the following formula (I) or pharmaceutically acceptable acid addition salt thereof, comprising reacting a compound of the formula (a) with a —C=X-providing agent selected from the group consisting of 1,1-carbonyldiimidazol, 1,1-carbonylthiodiimidazol, phosgene, thiophosgene, carbonyldiphenoxide, and phenylchloroformate to give a compound of the formula (b), reacting the compound of the formula (b) with a compound of the formula (c) to give a compound of the formula (I), and optionally converting it to an acid addition salt therof

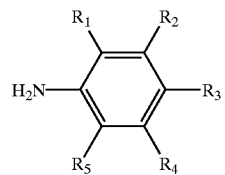

(a)

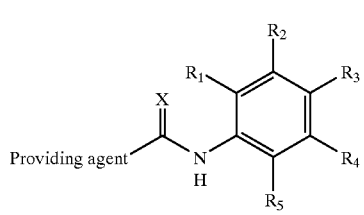

(b)

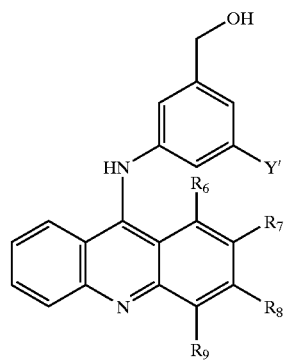

(C)

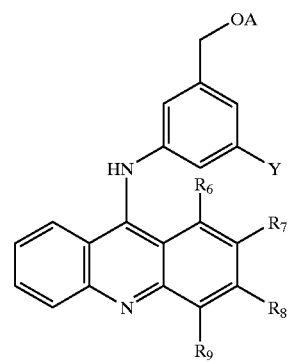

(I)

wherein, $R_1$, $R_2$, $R_3$, $R_4$, $R_5$, $R_6$, $R_7$, $R_8$, $R_9$, R' and Y are as defined in claim 1, and Y' is H or —$NH_2$.

3. A process for the preparation of a compound of the following formula (I) of claim 1 wherein Y is —N=CHR' or a pharmaceutically acceptable salt thereof, comprising reacting a compound of the general formula (d) with HCOR' in the presence of a base and an organic solvent to give a compound of the general formula (I)

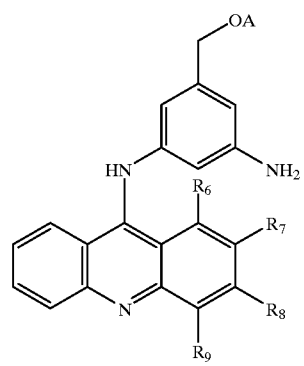

(d)

-continued (I)

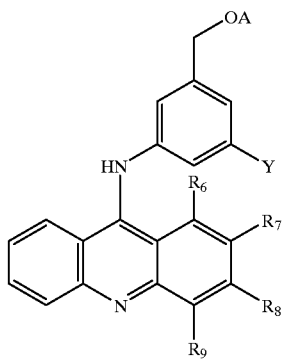

wherein, $R_6$, $R_7$, $R_8$, $R_9$, R', and A are as defined in claim 1.

4. A process for the preparation of a compound of the following formula (I) of claim 1 wherein Y is —NHC(O)CHR"NHR'" or a pharmaceutically acceptable addition salt thereof, comprising reacting a compound of the general formula (d) with

in the presence of a base and an organic solvent to give a compound of the general formula (I)

(d)

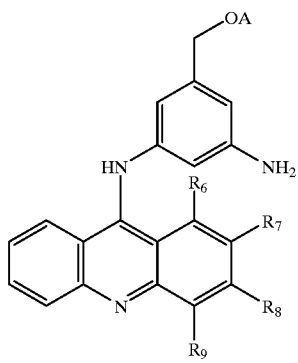

(I)

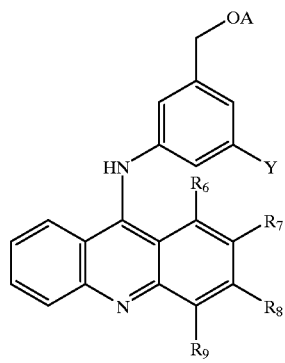

wherein, $R_6$, $R_7$, $R_8$, $R_9$, R", R'", and A are as defined in claim 1.

* * * * *